US00PP27325P3

(12) United States Plant Patent
Lyrene

(10) Patent No.: US PP27,325 P3
(45) Date of Patent: Nov. 1, 2016

(54) BLUEBERRY PLANT NAMED 'FL98-423'

(50) Latin Name: ***Vaccinium corymbosum* L.**
Varietal Denomination: FL98-423

(71) Applicant: Florida Foundation Seed Producers, Inc., Marianna, FL (US)

(72) Inventor: Paul M. Lyrene, Micanopy, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 66 days.

(21) Appl. No.: 14/544,723

(22) Filed: Feb. 9, 2015

(65) Prior Publication Data

US 2015/0237776 P1 Aug. 20, 2015

(30) Foreign Application Priority Data

Feb. 14, 2014 (QZ) ..... PBR 2014/0348

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP10,788 P 2/1999 Lyrene
PP19,503 P3 11/2008 Lyrene

OTHER PUBLICATIONS

Firmness and Storage Characteristics of Crisp-Textured Blueberries, Les Padley Jr., Thesis, University of Florida, 2005, pp. 1-74.*

* cited by examiner

*Primary Examiner* — Anne Grunberg
(74) *Attorney, Agent, or Firm* — Dentons US LLP

(57) ABSTRACT

'FL98-423' is a new and distinct southern highbush blueberry (*Vaccinium corymbosum* L.) variety distinguished by a very low chilling requirement, upright growth habit, and fruit that are large, firm, sweet, with a small, dry picking scar.

6 Drawing Sheets

Latin name of the genus and species of the plant claimed: *Vaccinium corymbosum* L.

Variety denomination: 'FL98-423'.

CROSS REFERENCE TO RELATED APPLICATIONS

This application claims the benefit of European Community Plant Breeders Rights Appl. No. 2014/0348, filed Feb. 14, 2014, herein incorporated by reference in its entirety.

BACKGROUND OF THE INVENTION

The present invention relates to a new and distinct hybrid variety of southern highbush blueberry (*Vaccinium corymbosum* L.) named 'FL98-423'. 'FL98-423' is a blueberry clone distinguished by its low chilling requirement, vigorous, upright bush, and very large, sweet, firm berries that ripen from early-February through late-March when grown under evergreen conditions. Several hundred plants of 'FL98-423' have been propagated by softwood stem cuttings in Gainesville, Fla. USA and near Lalla Mimouna, Morocco, and the resulting plants have all been phenotypically indistinguishable from the original plant. Contrast is made to 'Snowchaser' (U.S. Plant Pat. No. 19,503), an important variety worldwide for evergreen production. The claimed plant is important because it has more upright growth and is less susceptible to fungal diseases than 'Snowchaser'.

'FL98-423' also has larger, firmer, and sweeter, low-acid fruit than 'Snowchaser' during a similar maturity period.

'FL98-423' originated as a seedling from a cross between 'FL95-52' (unpatented) as the female (seed) parent and 'Santa Fe' (U.S. Plant Pat. No. 10,788) as the male (pollen) parent. This cross was made as part of a breeding program in a greenhouse in Gainesville, Fla. USA, in February 1995. The seedling was planted in a high-density field nursery in May 1996, and the first fruit were evaluated in April 1997. After the second year of fruiting in the field, in the spring of 1998, 'FL98-423' was asexually propagated by softwood stem cuttings in Citra, Fla., and an experimental 15-plant test plot was established as part of a variety test in Windsor, Fla. USA, in January 1999. Based on the growth, yield, and fruit quality of this plot, 'FL98-423' was repropagated by softwood stem cuttings and experimental test plots ranging from 50 to several hundred plants were established in Windsor, Fla. USA and near Lalla Mimouna, Morocco. These plots have been observed during flowering and ripening each year, and no mutations or off-type plants have been observed.

'FL98-423' differs from the proprietary parent 'FL95-52' (unpatented) in that 'FL98-423' has a greater tendency toward evergreeness and larger fruit. 'FL98-423' differs from the parent 'Santa Fe' (U.S. Plant Pat. No. 10,788) in that 'FL98-423' has a greater tendency toward evergreeness and has larger fruit. 'FL98-423' differs from the commercial variety 'Snowchaser' (U.S. Plant Pat. No. 19,503), an important variety planted worldwide for early production, in that 'FL98-423' has more upright growth and is less susceptible to *Botrytis* fruit rot and powdery mildew (*Microsphaera vaccinia*) than 'Snowchaser'. 'FL98-423' also has larger, firmer, and sweeter, low-acid fruit than 'Snowchaser' during a similar maturity period.

SUMMARY OF THE INVENTION

Blueberry variety 'FL98-423' exhibits outstanding and distinguishing characteristics when grown under evergreen horticultural practices in Morocco, including:

(1) a vigorous, upright bush;
(2) early ripening (50% ripe berries in Morocco around March 25); and
(3) large, sweet, low-acid, firm berries with a small, dry picking scar.

BRIEF DESCRIPTION OF THE DRAWINGS

The accompanying photographs show typical bush, flower, and fruit characteristics for 'FL98-423'. Colors shown are as true as can be reasonably reproduced by photographic procedures and may differ from those cited in the detailed description, which accurately describes the colors of 'FL98-423'.

DETAILED BOTANICAL DESCRIPTION

Figure 1:
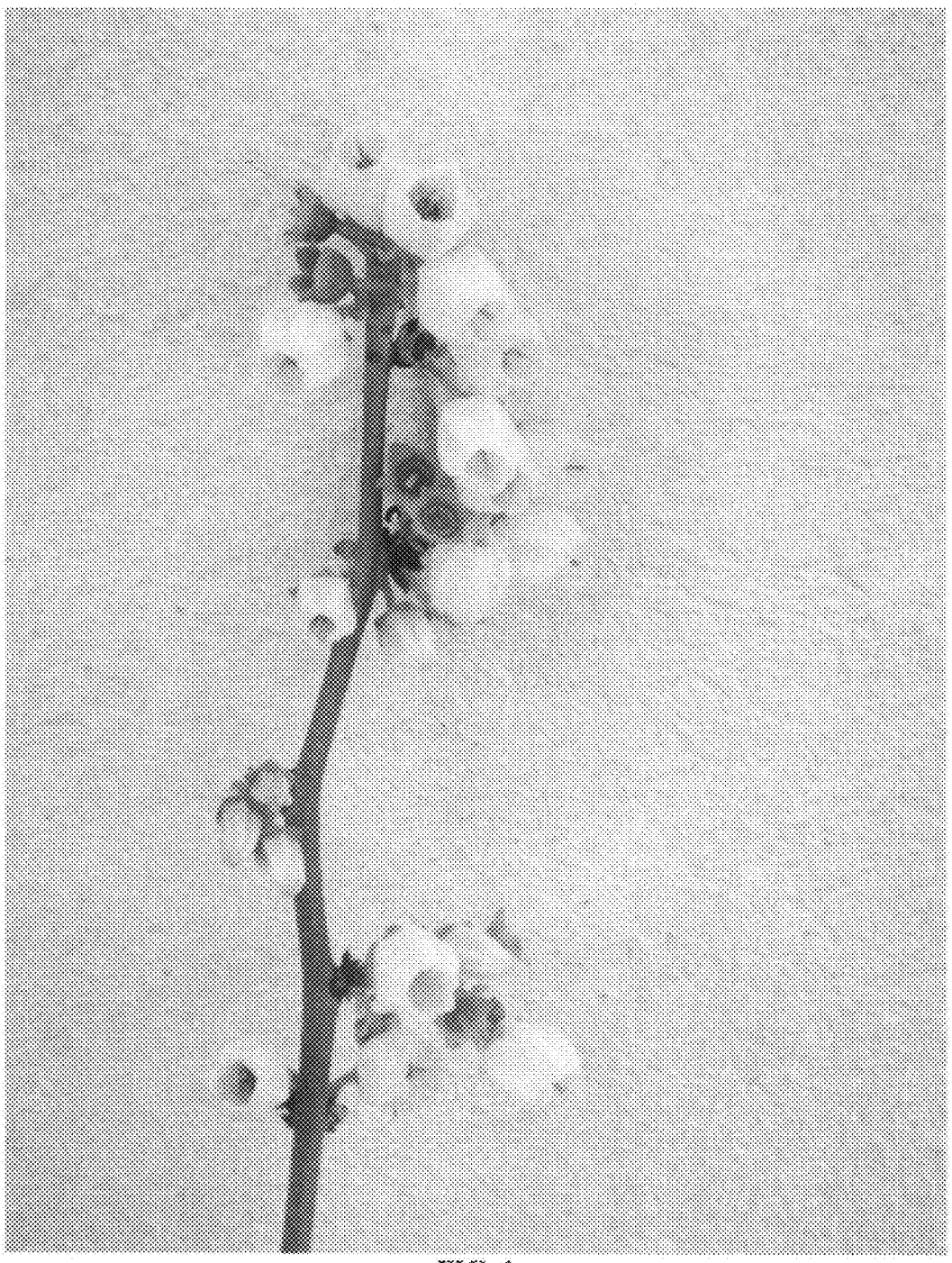
FIG. 1—Shows several clusters of opening 'FL98-423' flowers during the early stages of flowering in March.
Figure 2:
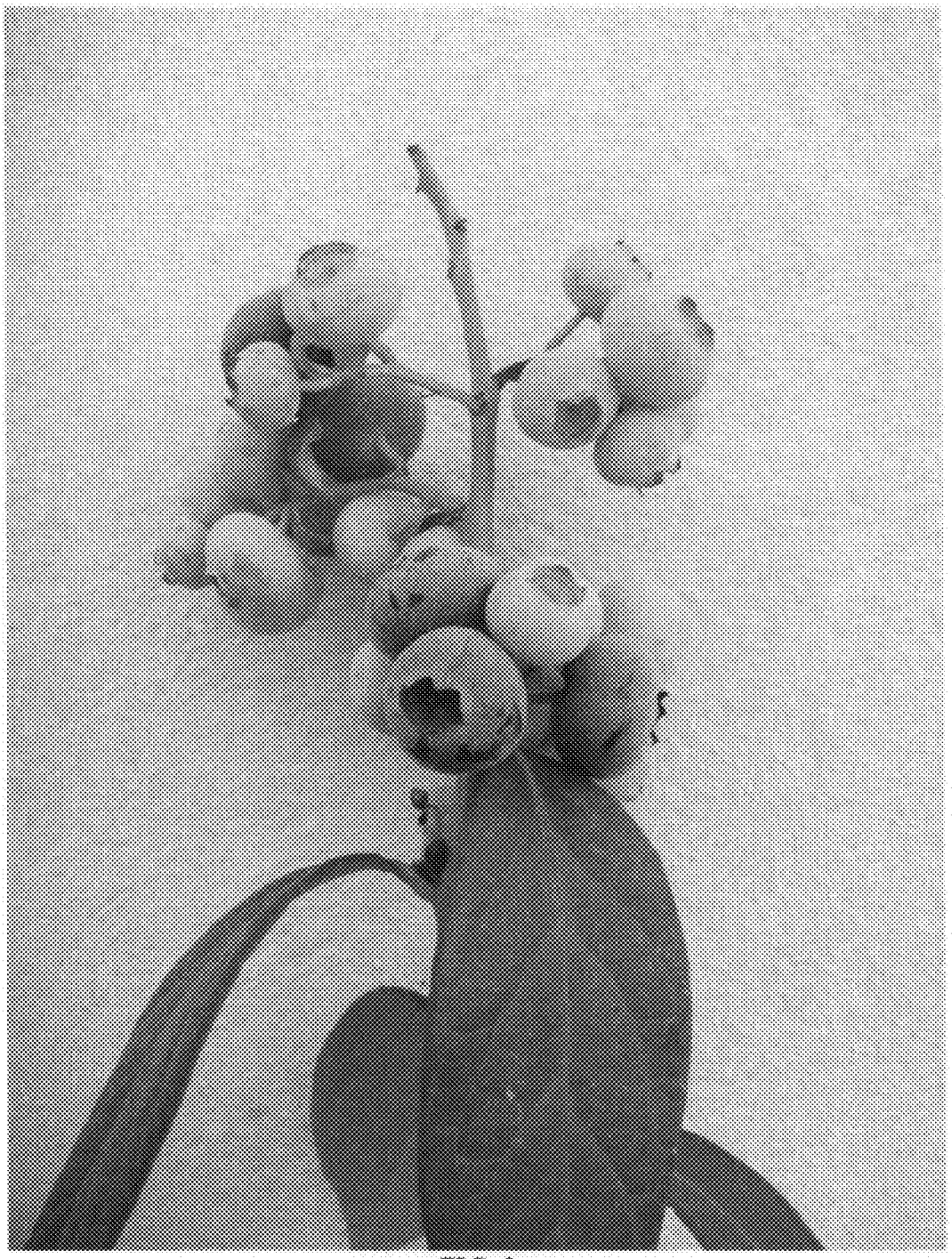
FIG. 2—Shows several clusters of 'FL98-423' berries during the fruit ripening season.
Figure 3:
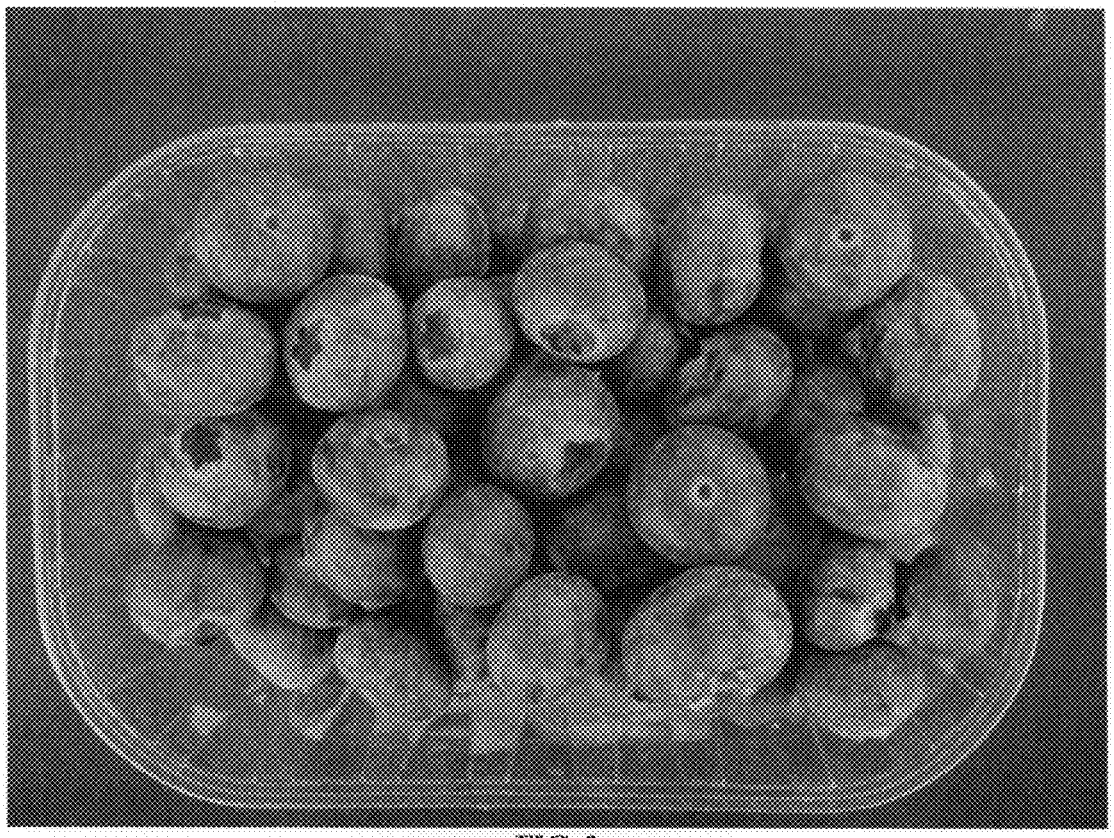
FIG. 3—Shows a close-up of harvested 'FL98-423' berries.
Figure 4:
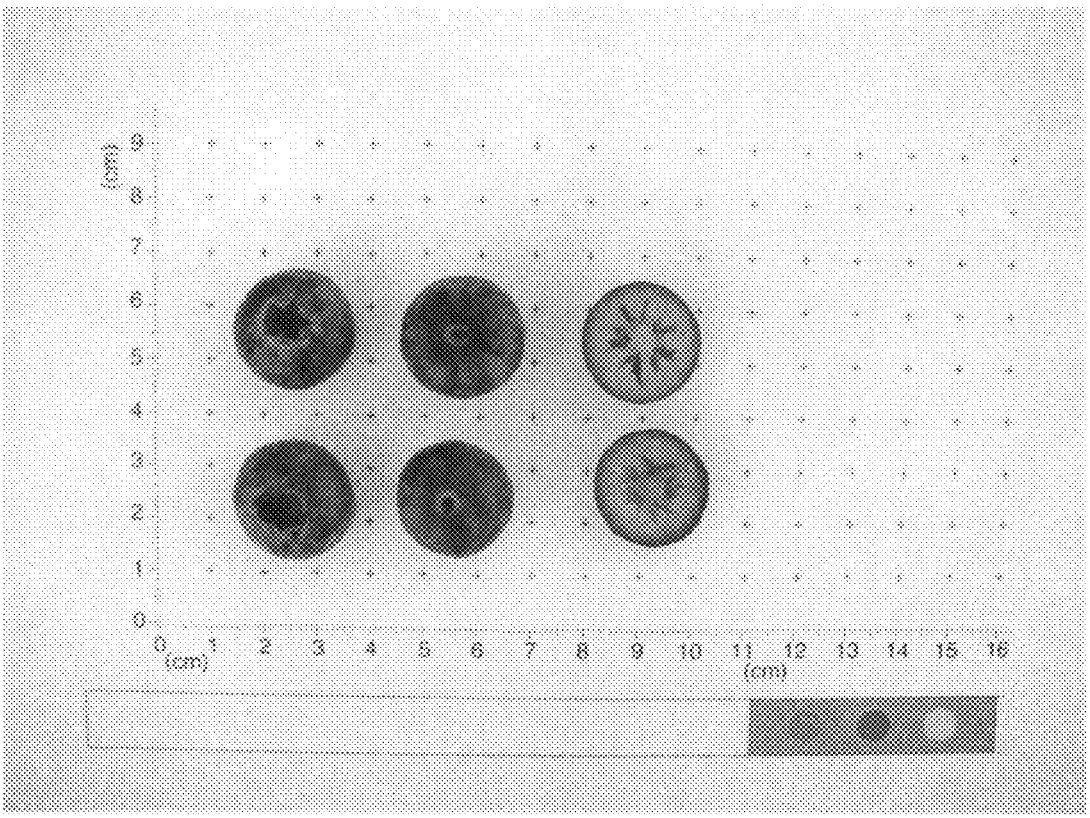
FIG. 4—Shows a close-up of mature 'FL98-423' fruit with a scale bar.
Figure 5:
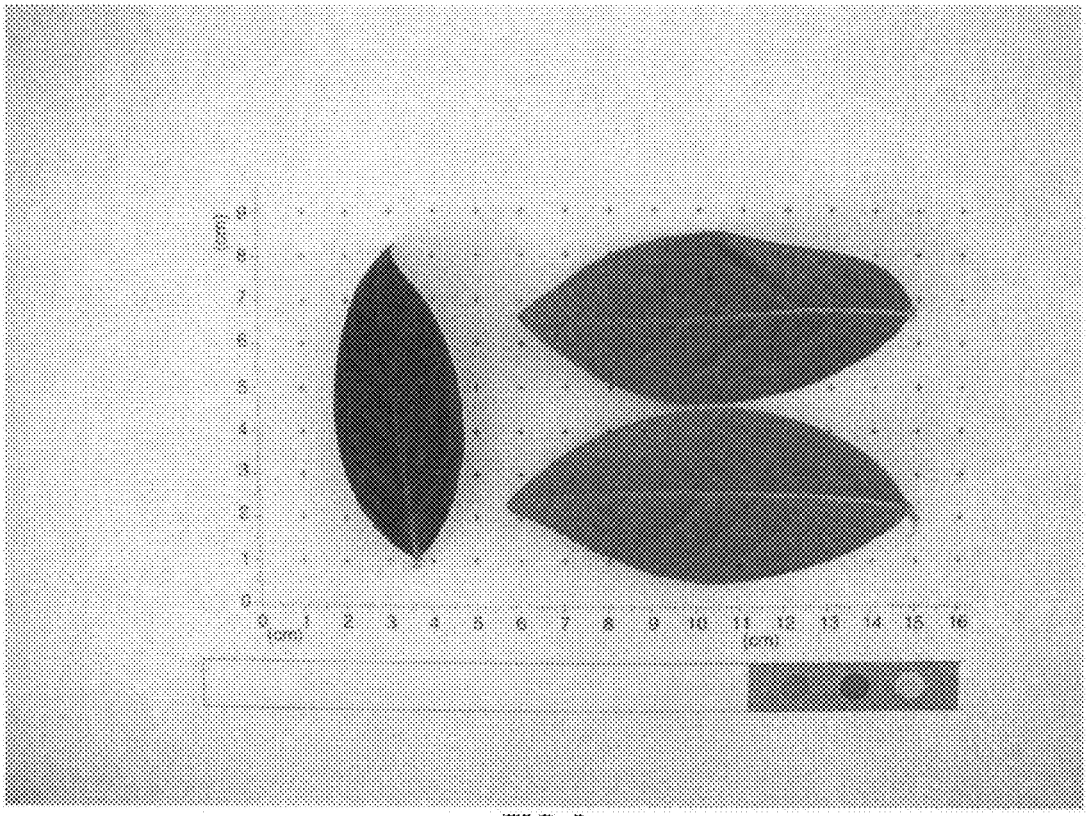
FIG. 5—Shows a close-up of 'FL98-423' leaves with a scale bar.
Figure 6:
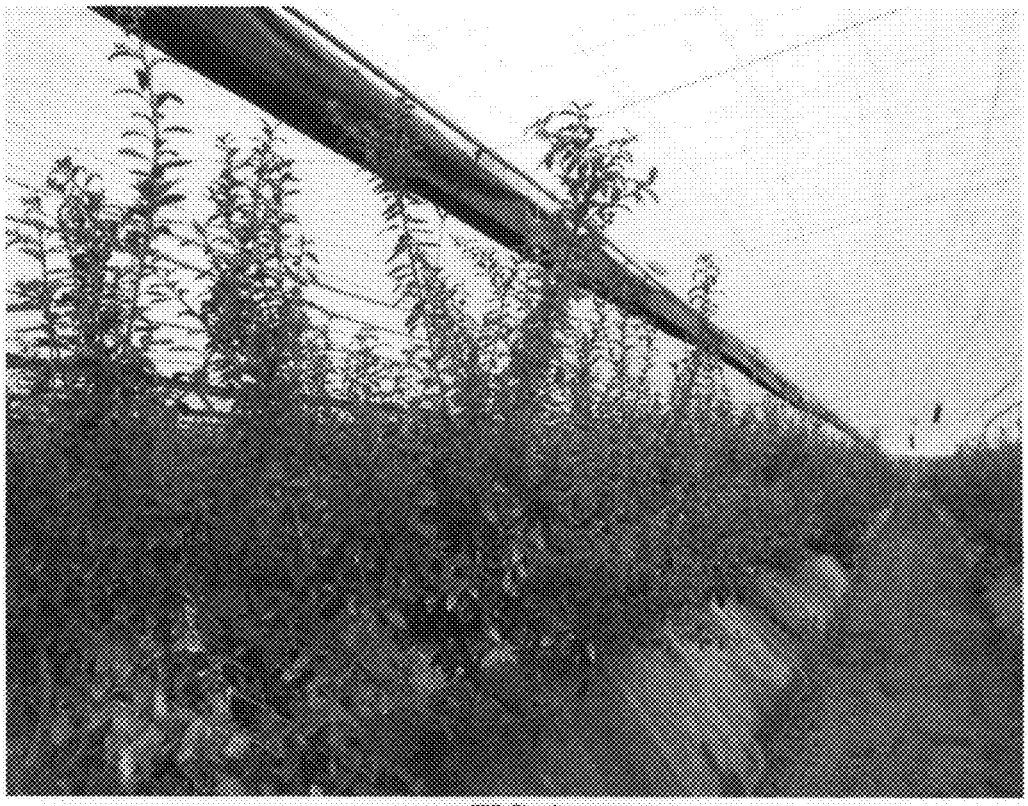
FIG. 6—Shows several two-year-old 'FL98-423' plants during the vegetative growth period near Lalla Mimouna, Morocco.

The following detailed description sets forth the distinctive characteristics of 'FL98-423'. The data that define these characteristics were collected from asexual reproductions carried out in Lalla Mimouna, Morocco. The plant history was taken on a plot of 50 seven-year-old plants growing in a commercial field near Lalla Mimouna, Morocco. Certain characteristics may vary with plant age. 'FL98-423' has not been observed under all possible environmental conditions, and the measurements given may vary when grown in different environments. Where means are given, the sample size was 20. Color descriptions are based on The Royal Horticultural Society (R.H.S.) Colour Chart by The Royal Horticultural Society, London, Fifth Edition, 2007. When the RHS color designations differ from the accompanying photographs, the R.H.S. color designations are accurate.

PHENOTYPIC DESCRIPTION OF *VACCINIUM CORYMBOSUM* L. ('FL98-423')

Plant:

*Plant vigor.*—High.
*Growth habit.*—Upright.
*Flower bud density (number) along flowering twigs in March.*—Medium to high.
*Twigginess.*—Low.
*Tendency toward evergreenness.*—High.
*Productivity.*—In trials in Morocco, 'FL98-423' was very productive, with higher total yields than 'Snowchaser' (U.S. Plant Pat. No. 19,503).
*Chilling requirement.*—'FL98-423' has performed best under evergreen production conditions where chilling is not calculated. 'FL98-423' flowered and leafed well in areas receiving an average of 300 chill hours (0 to 7° C.) when trialed in Florida, USA as a deciduous plant.
*Cold hardiness.*—'FL98-423' has not been grown in temperate climates with extremely cold winter temperatures. Plants have survived winter freezes of −6° C. with minimal damage.
*Ease of propagation.*—'FL98-423' has only been propagated from softwood stem cuttings, where the rooting percentage is typically less than other varieties.

Trunk and branches:

*Suckering tendency.*—Low. Three-year-old plants typically have 3 to 7 major canes arising from a crown 30 cm in diameter.
*Surface texture (of strong, 6-month-old shoots observed in March).*—Smooth.
*Surface texture (of 3-year-old and older wood).*—Rough.
*Color of new twigs observed in the field.*—Yellow-green N144D.
*Color of 3-year-old, rough-textured canes.*—Greyed-brown 199D.
*Internode length (strong, upright shoots measured in March).*—Mean of 23.5 mm.

Leaves:

*Length (including petiole, from tip of petiole to end of blade).*—Mean of 9.2 cm.
*Width (at widest point).*—Mean of 3.9 cm.
*Shape.*—Elliptic, with an attenuate base and acute tip.
*Margin.*—Entire.
*Color.*—Upper surface: Green N137B. Lower surface: Yellow-green 147B.
*Pubescence.*—Upper surface of leaves: Absent. Lower surface of leaves: Absent. Margins: Absent.
*Relative time of leafing versus flowering.*—When grown as an evergreen plant, leafing is delayed relative to flowering.

Flowers:

*Arrangement.*—Flowers are arranged alternately along a short, leafless, deciduous branch.
*Fragrance.*—Strong floral fragrance.
*Shape.*—Urceolate.
*Flowering period.*—The bloom period when observed under evergreen production in Morocco is from October to December.
*Cluster (tight, medium, loose).*—Loose.
*Number of flowers per cluster.*—Mean of 5.3.
*Pedicel.*—Length at time of anthesis: Mean of 6.9 mm. Color at time of anthesis: Yellow-green 145B with Greyed-red 180C on sun-exposed side.
*Peduncle.*—Length at time of anthesis: Highly variable, mean of 14.6 mm. Color at time of anthesis: Yellow-green 150C with Greyed-red 180C on sun-exposed side.
*Calyx.*—Surface texture: Smooth and waxy. Diameter: Mean of 6.8 mm. Color: Blue-green 122B to Green 138D on tips of calyx lobes.

*Corolla.*—Diameter: Mean of 9.1 mm. Length (from pedicel attachment point to corolla tip excluding the pedicel): Mean of 12.4 mm. Aperture diameter: Mean of 5.1 mm. Texture: Smooth. Color: White 155C.

Reproductive organs:

*Style.*—Length (top of ovary to stigma tip): Mean of 11.6 mm. Color: Yellow-green 145B. Location of tip of stigma relative to lip of the corolla — Stigma tip is approximately 1 mm outside or even with the corolla lip.

*Anthers.*—Color: Greyed-orange 167B.

*Pollen.*—Abundance of shed: Medium. Color: Orange-white 159C.

*Self-fruitfulness.*—Low to medium. Planting in field configurations that promote cross fertilization with other southern highbush varieties is recommended for all southern highbush blueberry plants.

Fruit: Mean date of 50% harvest near Lalla Mimouna, Morocco is March 25.

*Diameter of calyx aperture on mature berry.*—Mean of 7.6 mm.

*Size and shape of calyx lobes on mature berry.*—Small lobes, flat. Medium calyx basin.

*Pedicel length on ripe berry.*—Mean of 9.0 mm.

*Detachment force for ripe berries* (*easy, medium, hard*).—Medium.

*Number of berries per cluster.*—Mean of 4.9.

Berry:

*Cluster* (*tight, medium, loose*).—Loose.

*Weight* (*on well-pruned plants*).—Mean of 3.3 g.

*Height.*—Mean of 13.8 mm.

*Width.*—Mean of 20.1 mm.

*Shape.*—Oblate.

*Surface color of mature berries ripe on the plant.*—Violet-blue 98D.

*Surface color of ripe berry after polishing.*—Greyed-purple N186A.

*Immature berry color, with bloom.*—Greyed-green 193D.

*Immature berry color without bloom.*—Yellow-green 144C.

*Surface wax.*—Medium to high. The surface wax on 'FL98-423' has only moderate persistence.

*Pedicel scar.*—Small and dry. Mean of 2.2 mm.

*Firmness.*—Firm.

*Flavor.*—Sweet, low acid, mild flavor.

*Texture.*—Smooth, juicy, small seeds, and no stone cells present.

Seeds:

*Color of dried seeds.*—Greyed-orange N167A.

*Length of well-developed dried seed.*—Mean of 2.2 mm.

*Width of well-developed dried seed.*—Mean of 1.3 mm.

Use: 'FL98-423' produces southern highbush blueberries suitable for fresh markets. 'FL98-423' has performed best in trials when grown under an evergreen management system.

Resistance to diseases, insects, and mites: 'FL98-423' has grown vigorously and shows excellent bush survival when grown under protected cultivation in an evergreen management system. It appears to be moderately resistant to root rot (*Phytophthora cinnamomi*). 'FL98-423' appears to have excellent resistance to the fungal species that cause summer leaf spots. Resistance of 'FL98-423' to fungal leaf spots, *Botrytis* fruit rot, and powdery mildew (*Microsphaera vaccinia*) is greater than that of 'Snow-chaser' (U.S. Plant Pat. No. 19,503).

What is claimed is:

1. A new and distinct southern highbush blueberry plant named 'FL98-423', as illustrated and described herein.

* * * * *